US010850047B2

(12) United States Patent
McCormick (10) Patent No.: US 10,850,047 B2
(45) Date of Patent: Dec. 1, 2020

(54) INSULATED STORAGE SYSTEM WITH BALANCED THERMAL ENERGY FLOW

(75) Inventor: Bruce McCormick, Sante Fe, NM (US)

(73) Assignee: SAVSU TECHNOLOGIES LLC, Old Bethpage, NY (US)

( * ) Notice: Subject to any disclaimer, the term of this patent is extended or adjusted under 35 U.S.C. 154(b) by 0 days.

(21) Appl. No.: 13/333,457

(22) Filed: Dec. 21, 2011

(65) Prior Publication Data

US 2012/0325826 A1    Dec. 27, 2012

Related U.S. Application Data

(60) Provisional application No. 61/425,544, filed on Dec. 21, 2010.

(51) Int. Cl.
*F25D 3/06* (2006.01)
*A61M 5/44* (2006.01)
*A61J 1/16* (2006.01)

(52) U.S. Cl.
CPC ............ *A61M 5/44* (2013.01); *F25D 3/06* (2013.01); *A61J 1/165* (2013.01); *F25D 2303/0844* (2013.01); *F25D 2303/0845* (2013.01); *F25D 2331/804* (2013.01); *F25D 2600/04* (2013.01)

(58) Field of Classification Search
CPC ..... F25D 3/02; F25D 3/06; F25D 3/08; F25D 3/10; F25D 3/102; F25D 3/105; F25D 3/107; B65D 1/18; B65D 1/38; B65D 1/3802; B65D 1/3804; B65D 1/3806; B65D 1/3809; B65D 1/3811; B65D 1/3813
USPC ... 62/326, 331, 371, 440, 451, 457.1, 457.2, 62/457.9, 464; 220/592.2, 592.23, 220/592.24, 592.25, 592.26, 592.15
See application file for complete search history.

(56) References Cited

U.S. PATENT DOCUMENTS

| | | | | |
|---|---|---|---|---|
| 4,003,214 A | * | 1/1977 | Schumacher | 62/340 |
| 6,070,427 A | * | 6/2000 | Fine et al. | 62/371 |
| 6,308,518 B1 | * | 10/2001 | Hunter | 62/3.3 |
| 6,457,323 B1 | * | 10/2002 | Marotta | 62/371 |
| 6,666,032 B1 | * | 12/2003 | Rickson et al. | 62/3.6 |

(Continued)

FOREIGN PATENT DOCUMENTS

| | | |
|---|---|---|
| EP | 0890525 | 1/1999 |
| JP | 55176178 | 12/1980 |

(Continued)

OTHER PUBLICATIONS

International Search Report for PCT/US2011/068589 dated Jul. 24, 2012, 3 pages.

*Primary Examiner* — Ana M Vazquez
(74) *Attorney, Agent, or Firm* — Brown & Michaels, PC (57) ABSTRACT

A storage system that includes a contents container and a thermal battery, each in thermal communication with a thermal moderator that is constructed and arranged to balance the thermal energy flow between the contents container and the environment with the thermal energy flow between the contents container and the thermal battery. The thermal moderator can include a super-insulating material, a phase change material and/or a heat pipe. The storage system may help to maintain stored contents within a desired temperature range for an extended period of time, while minimizing the likelihood of damage to the contents due to an initial temperature of the thermal battery being outside of the desired temperature range.

28 Claims, 2 Drawing Sheets

(56) References Cited

U.S. PATENT DOCUMENTS

| | | | |
|---|---|---|---|
| 7,908,870 B2* | 3/2011 | Williams et al. | 62/62 |
| 2004/0079794 A1* | 4/2004 | Mayer | 229/103.11 |
| 2006/0191282 A1* | 8/2006 | Sekiya et al. | 62/371 |
| 2008/0135564 A1* | 6/2008 | Romero | 220/592.2 |
| 2010/0018981 A1 | 1/2010 | Hyde et al. | |
| 2011/0308271 A1* | 12/2011 | Schryver | 62/465 |

FOREIGN PATENT DOCUMENTS

| | | |
|---|---|---|
| JP | 01308785 | 12/1989 |
| JP | 2005195296 | 7/2005 |

* cited by examiner

INSULATED STORAGE SYSTEM WITH BALANCED THERMAL ENERGY FLOW

CROSS REFERENCE TO RELATED APPLICATION

This application claims the benefit of Provisional Application No. 61/425,544, filed Dec. 21, 2010, the entire contents of which are hereby incorporated by reference.

TECHNICAL FIELD

The present disclosure relates generally to thermally insulated storage containers and, more particularly, to storage containers that can maintain their contents within a particular temperature range for an extended period of time.

BACKGROUND

Thermally insulated storage containers can provide a storage area that may slow the temperature change of its contents, either by slowing the loss of thermal energy from the storage area to a cooler exterior environment, or by slowing the transfer of thermal energy from a warmer exterior environment to the storage area and its contents. While certain uses of insulated storage containers are mainly for convenience or comfort, such as keeping beverages warm or cool for longer periods of time without refrigeration, other uses of insulated storage containers may be critical to prevent damage and/or loss of important contents such as medicines, vaccines, biological materials, spoilable food product, or organs awaiting transplant, to name a few. Unlike a beverage that can be cooled again if the storage container allows it to become too warm to enjoy, some goods having biological materials may have living components or tissue that cannot be brought back to life once they fall outside a particular temperature range. Even certain medicines and vaccines that do not contain biological materials may include chemical compositions that become unstable outside a particular temperature range and cannot be restabilized. For example, some such materials must be kept continuously at temperatures ranging from 2° C. to 8° C., a relatively narrow temperature range above which degradation of the materials can occur, and below which destruction by freezing can occur.

Because these types of temperature sensitive materials can often be expensive to produce and replace, losses due to inadequate temperature maintenance can be excessive economically, reduce adequate access to medicines by those in need of them, or in some cases can be the difference between life and death. Compounding these problems is the fact that oftentimes the populations of the world that are most in need of medicines and vaccines, for example, are located in remote and/or underdeveloped areas. It is often the case that electrically powered refrigeration is unlikely to be widely available in such areas. In these instances, available electrical refrigeration units may be many miles from one another, requiring transport without refrigeration for extended periods of time. Even where refrigerated transportation means are available, local refrigerated storage at destinations in some underdeveloped areas of the world may be subject to frequent power outages, voltage spikes, generator fuel shortages, and damaged or poorly maintained equipment. Thermally insulated storage containers may be used to maintain their contents within particular temperature ranges in these or other instances of temporary absences of powered refrigeration.

SUMMARY

According to one embodiment, a storage system is provided that may include a contents container, a thermal battery, and a passive thermal moderator. The contents container includes a storage area for temperature-sensitive items, and the thermal battery includes thermal mass for increasing the total heat capacity of the storage system. The passive thermal moderator is in thermal communication with the storage area of the contents container and with the thermal battery and regulates the thermal energy flow between the contents container and the thermal battery. The thermal energy flow between the contents container and the thermal battery is substantially balanced with the thermal energy flow between the contents container and an environment outside of the storage system by the thermal moderator. A desired temperature may thereby be maintained in the storage area of the contents container.

According to another embodiment, a storage system is provided that may include a contents storage area, a thermal mass storage area, a plurality of walls, and a passive thermal moderator. The contents storage area is provided for holding temperature-sensitive items, and the thermal mass storage area is provided for holding thermal mass. The thermal mass storage area is separate from the contents storage area. The plurality of walls may be arranged to isolate each of the storage areas from an environment outside of the storage system, and each wall may include a layer of insulating material. The thermal moderator is provided for transferring thermal energy between the two storage areas and from one side of a layer of super-insulating material to an opposite side of the layer of super-insulating material. The thermal moderator may have a pre-determined thermal energy flow rate that approximates a thermal energy flow rate between the environment outside of the storage system and the contents storage area when the thermal mass storage area includes thermal mass at a known phase change temperature.

BRIEF DESCRIPTION OF THE DRAWINGS

One or more preferred exemplary embodiments of the invention will hereinafter be described in conjunction with the appended drawings, wherein like designations denote like elements, and wherein.

DETAILED DESCRIPTION OF THE PREFERRED EMBODIMENT(S)

Thermally insulated storage containers may generally be categorized as either active storage containers or passive storage containers. Active storage containers typically include some type of refrigeration or heating device that converts some other type of energy, such as electrical energy, into thermal energy to be either transferred into a storage area of the storage container or to be used to extract thermal energy out of the storage area. Passive storage containers, on the other hand, typically do not rely on any such external device, instead relying on thermally insulating materials and/or thermal mass to maintain storage area temperatures within a given range. Thermal mass, as is sometimes used with passive storage containers—particularly for maintaining storage area temperatures below normal atmospheric temperatures—may be in the form of wet ice, dry ice, cold packs of water or gel, and/or phase change materials. Generally, thermal mass materials work on the principle of increasing the overall heat capacity of the storage area of the container so that more energy exchange is required between the storage area and the exterior environment to change the temperature of the storage area by a particular amount. Where a container is constructed such that it allows a given amount of thermal energy transfer into or out of its storage area, an increased thermal mass in the storage area may extend the amount of time that the storage area will remain within the desired temperature range. This amount of time that the storage area of a passive container remains in the desired temperature range may also be known as the "autonomy" of the container.

Providing additional thermal mass in the storage area of a storage container to provide the desired level of autonomy can be a useful method with contents that must be kept near 0° C. because wet ice (solid water) can be used as a phase change material near that temperature. Water has a relatively high heat of fusion compared to some other materials that change phases in the same general temperature range, and therefore requires relatively large amounts of thermal energy per unit mass to change it from its solid ice phase to its liquid water phase. Water also has the advantage of being relatively plentiful and inexpensive. However, wet ice can sometimes result in difficulties that are particular to biological or related materials.

For example, depending on the amount of time the stored contents must be kept within the desired temperature range, it may be necessary to include additional thermal mass in the storage area of the container that is in an amount that is two to four the mass of the stored contents, or more. As the amount of thermal mass increases in relation to the mass of the stored contents, the risk of inadvertent freezing or over-cooling of the contents also increases. In other words, 0° C., which is the temperature at which the solid-to-liquid phase change occurs for water, may be outside of the desired range of the contents. For example, certain biological and/or chemical materials may need to be maintained in the range of 2-8° C. For such contents, it is possible that, after extended periods of time in the same storage area as the wet ice, enough thermal energy will be removed from the contents that they will fall below 2° C. and/or freeze, particularly where the contents include any water in their compositions. Also, because of the fact that wet ice is at 0° C. while melting, it typically must be carefully packaged with specialized care in relation to the contents, because direct contact between the contents and the ice creates a thermally conductive path which can cause a rapid decrease in the temperature of the contents and result in freezing of the contents. A related concern is that the storage container and its contents, in instances when it is subjected to search or inspection by customs agents or others who are untrained in the careful packaging techniques, may not be repackaged properly, leading to inadvertent freezing of the contents.

Another concern is that when wet ice is first placed into the storage container, it is normally below its melting point—i.e., it is typically frozen and stored at a lower temperature, such as about −20° C. This amplifies all of the other concerns, as the higher temperature differential between the contents and the ice accelerates the energy loss of the contents. Because storage containers may be constructed with super-insulating materials to isolate the storage area from the exterior environment, it may sometimes require a substantial amount of time for the ice to reach its melting point, thereby extending the time that the contents are exposed to sub-zero temperatures. The storage systems and methods described below address some of these issues by providing separate storage areas for the stored contents and for the thermal mass and by providing thermal moderators to enable the transfer of thermal energy between the storage areas in a predictable and controlled manner.

As used herein, the term "insulating," where used to describe materials and/or elements of storage containers or systems, broadly describes all types of materials or elements that may typically function to thermally insulate different areas of the containers or systems from one another or from an exterior environment. While theoretically almost any material can provide at least some level of thermal insulation, "insulating" in the context of thermally insulated containers or systems is generally used to describe materials or elements having a thermal conductivity of 0.1 W/m-K or less. Exemplary insulating materials that are not super-insulating include polymeric materials having foamed or expanded structures, such as expanded polystyrene (EPS) or polyurethane foam, or other non-polymeric materials, such as fiberglass, asbestos, and various gases such as air, oxygen, or nitrogen, for example. The term "super-insulating," as used herein, and where used to describe materials and/or elements of storage containers or systems, generally describes materials or elements having a thermal conductivity of less than 0.02 W/m-K. Therefore, super-insulating materials or elements are a subset of insulating materials or elements such that all super-insulators are insulators, but not all insulators are super-insulators. Some examples of materials that may be super-insulating include aerogel materials, microporous materials, vacuum panels and some gases, such as argon (Ar), xenon (Xe), or carbon dioxide ($CO_2$), for example.

Figure 1:
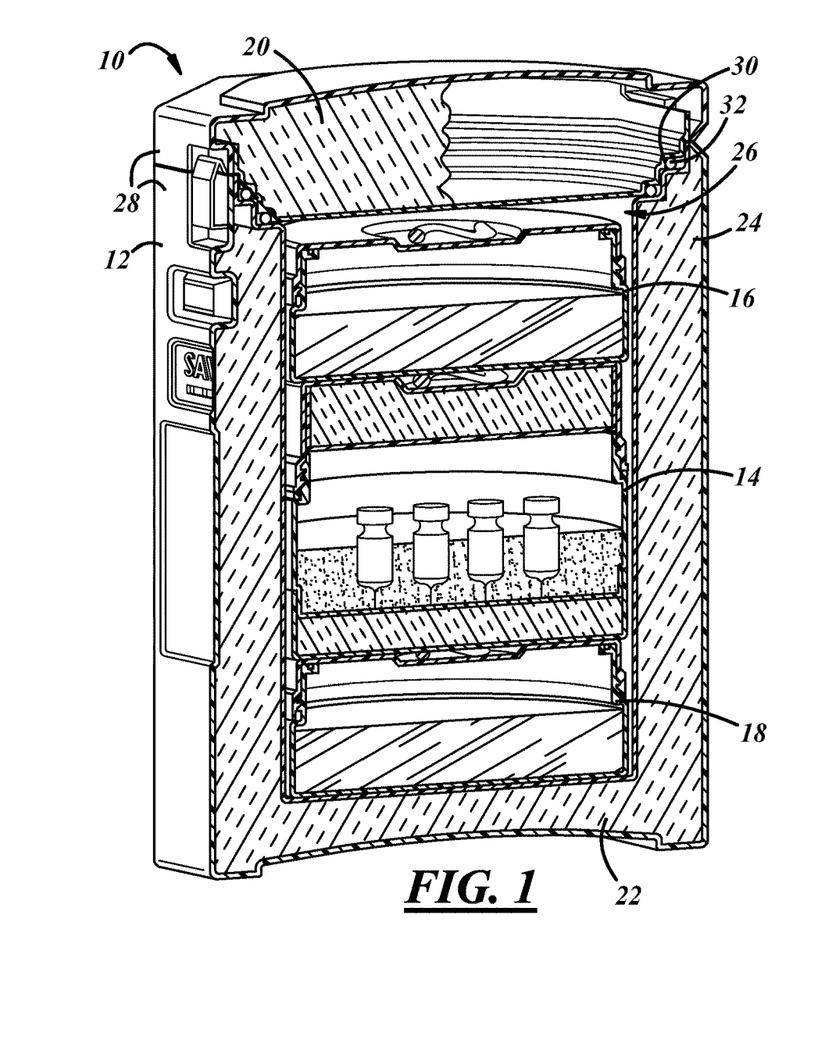
FIG. 1 is a cut-away view of an exemplary storage system according to one embodiment, showing thermal moderators in thermal communication with a contents container and two thermal batteries.

Referring now to FIG. 1, a cut-away view of an exemplary storage system 10 is shown. In this embodiment, the storage system 10 includes a thermally insulated storage container 12, a contents container 14, and thermal batteries 16, 18. Storage container 12 includes a top wall 20, a bottom wall 22, and one or more side walls 24. When top wall 20 is closed, a storage area 26 is defined by surfaces of the walls 20-24. The container may also include a protective case 28, as shown. In this example, case 28 is in two pieces, with a bottom piece housing the bottom and side walls 22, 24 and a top piece housing the top wall 20. Protective case 28 may be constructed from any durable material sufficient to protect the various walls from damage during shipment and handling, such as a metal, rigid plastic, composite, or other suitable material. It may also include various hardware as shown, such as handles, latches, hinges, etc.

Walls 20-24 may be constructed to include any of a variety of insulating materials, preferably including super-insulating materials or elements such as aerogel panels, microporous insulating materials, vacuum panels, or super-insulating gas-filled panels. Any combination of super-insulating materials and non-super-insulating materials may be used, such as multiple overlapping layers of super-insulating materials encased in polyurethane foam, for example. Alternatively, any of walls 20-24 may be made entirely from lower cost non-super-insulating materials such as expanded polystyrene (EPS). The thermal conductivity of any type of material or the R-value of any combined thicknesses of materials may be taken into account in the storage system structures and methods described herein. The bottom and side walls 22, 24 may be unitary as shown, or they may be separate pieces attached together. Any joint between the various walls 20-24 of the container 12 may include complimentary edges 30, such as those shown at the joint between top and side walls 20, 24. The edges 30 shown include a complex edge profile—in this case, a step-shaped profile—to increase the length of the thermal leak path at the joint. Additional description regarding the use and benefits of container walls having complex edge profiles and thermal leak paths of increased length, along with different configurations of storage container walls that include overlapping layers of super-insulating materials, is discussed in commonly-owned US Patent Application Publication No. 2012/0318808, the entire contents of which are hereby incorporated by reference.

This particular embodiment of storage container 12 includes seals or O-rings 32 at the joint between the top and side walls 20, 24. Storage area 26 is sized and shaped to accommodate the contents container 14 and thermal batteries 16, 18. In the embodiment of FIG. 1, storage area 26 is cylindrical to accommodate the cylindrical container 14 and batteries 16, 18. Of course, the depicted storage container 12 is only exemplary in nature and may be shaped and sized in countless ways to define a storage area for holding at least a contents container and at least partially surrounding the contents container with thermally insulating walls.

Figure 2:
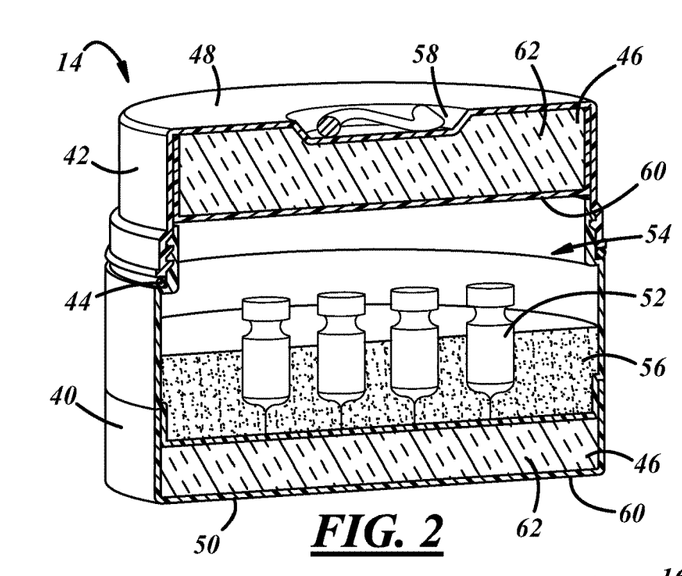
FIG. 2 is an enlarged view of the contents container and thermal moderators of FIG. 1.

FIG. 2. is a cut-away view of exemplary contents container 14. Contents container 14 is a container for holding temperature-sensitive items. In this embodiment, container 14 is cylindrical in shape and sized to closely fit within the cylindrical storage area 26 of FIG. 1. Contents container 14 may include a body 40, a cover 42, an optional seal 44, thermal moderators 46, and thermal communication areas 48, 50. The body 40 is the main portion of the container 14 and holds contents 52, such as the vials shown, in a storage area 54. In this example, an insert 56 is provided in the storage area to secure the contents 52 in place. Insert 56 may be a soft foam material having slits or other openings in that snugly surround contents 52 as shown. Of course, contents of various shapes and sizes other than the vials shown may be held in the storage area with or without insert 56, and insert 56 may include various sizes of cut-outs to secure different shapes of contents 52 and is not limited to a soft foam material.

Cover 42 can be removably placed over the open top of body 40 to physically isolate the storage area 54 from the surroundings of contents container 14. Cover 42 may also include a depression or recess 58 in its top surface as shown to accommodate a fold-down handle or similar component that may be grasped to lift the contents container 14 out of the storage container. The diameter or width of recess 58 may be sized to provide a known surface area for thermal communication area 48, for reasons discussed below. The body and cover 40, 42 may include complimentary threads for temporary screw-on attachment with each other as shown, but other temporary attachments may be used, such as snap or friction fits, latches, tamper-evident tape, or other types. In one embodiment, the contents container includes a locking mechanism or other secure closure to limit contents access to authorized personnel. Both the body 40 and the cover 42 can be made from various materials, depending on many factors such as cost, weight, security concerns, or other factors. In one embodiment, each is made from an olefin-based material such as high-density or low-density polyethylene. Seal 44 may be included as a fluid barrier to isolate the storage area 54 and its contents 52 from the environment outside of contents container 14 and/or to help prevent any gases that may be produced by the contents from escaping the container 14. In this example, seal 44 is an O-ring located at a bottom edge of the cover 42 when the cover is in place on the body 40, but it may be placed in various functional locations or omitted.

Thermal moderators 46 are included with contents container 14 in this particular embodiment and are provided to facilitate a controlled flow of thermal energy between the thermal batteries of the storage system and the contents container 14 or, more particularly, the storage area 54 of contents container 14. In the embodiment shown in FIG. 2, one thermal moderator 46 is shown attached at the bottom of contents container body 40, and another thermal moderator 46 is shown attached to the cover 42. Each exemplary thermal moderator 46 includes a body 60 that at least partially encloses a moderator material 62. In this embodiment, each body 60 is attached to one of the contents container components, contents container body 40 or cover 42, and holds the moderator material 62 adjacent its respective contents container component and adjacent storage area 54. Each body 60 may be removably attached to its respective container component as shown via a press, snap, or other type of fit for changing or performing maintenance on the moderator material 62, or it may be permanently attached.

Moderator material 62 includes a material or materials provided to slow or otherwise control the thermal energy transfer between the contents container and the thermal batteries, particularly during a temperature transition of the thermal battery from an initial temperature to a phase change temperature, as will be described in further detail below. Moderator material 62 may include an insulating material and/or a phase change material. In one embodiment, moderator material 54 includes a super-insulating material, such as an aerogel material, along with a pre-determined amount of water as a phase change material. These types of moderator materials 62 are passive in nature, making thermal moderators 46 passive thermal moderators, meaning that the moderators are designed to control thermal energy flow without the use of any type of electrical or other power source.

Each of thermal communication areas 48, 50 is provided as an interface between the thermal moderators 46 and the thermal batteries of the storage system, such as thermal batteries 16, 18 of FIG. 1. In the embodiment of FIG. 2, thermal communication area 48 is the top surface of the contents container 14 or cover 42, and thermal communication area 50 is the bottom surface of the contents container 14 or the body 60 of the lower thermal moderator shown in the figure. Each of these communication areas has a known surface area for use in determining thermal energy flow rates into and out of the contents container 14.

The particular contents container shown in FIG. 2 is only exemplary and can take other forms. For example, the thermal moderators 46 may be separate components from the contents container and be modular in nature, or they may be attached to the thermal batteries. In one embodiment the thermal moderators may be disc-shaped articles that include a moderator material as described and that can be disposed between the contents container and the thermal batteries. Other variations are possible that place thermal moderators between the contents container storage area 54 and the thermal batteries of the storage system to control the thermal energy flow therebetween.

Figure 3:
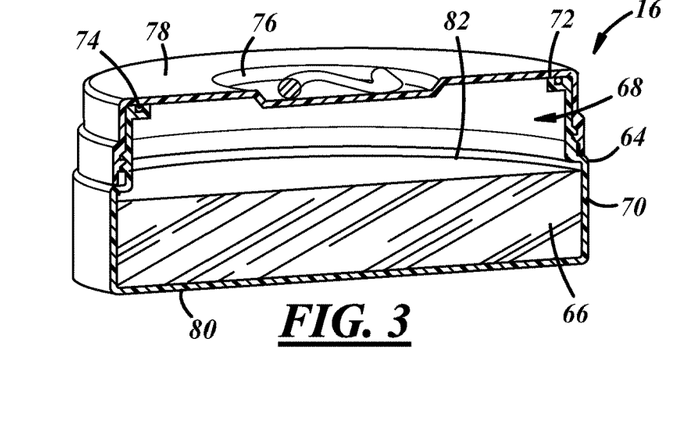
FIG. 3 is an enlarged view of one of the thermal batteries of FIG. 1.

FIG. 3. is a cut-away view of an exemplary upper thermal battery 16, which may be the same as lower thermal battery 18 as shown in FIG. 1 so that they are modular in nature and may be exchanged into or out of the storage container 12 as necessary. In use, the thermal battery 16 includes battery container 64 and thermal mass 66 included in a thermal mass storage area 68. Battery container 64 is somewhat similar to contents container 14 of FIG. 2, having a body 70 and a cover 72 that is removably attached to the body (again with a threaded connection in the particular embodiment shown), an optional seal 74, and a depression 76 in the top surface of the cover to accommodate a handle to lift the battery container 60 out of the storage container. As with the contents container, various body-to-cover attachments are possible and the optional seal may be located elsewhere between body 70 and cover 72. Top and bottom surfaces 78 and 80 are provided and may be thermal communication areas when positioned to be in contact with one of the thermal communication areas of the contents container, as described in conjunction with FIG. 2. Body 70 may include a fill-line 82 marked or molded into it to indicate the fill-level for the thermal mass 66. For example, thermal mass 66 may be wet ice, as depicted, and may be formed in the battery container 64 by filling the body 70 to the fill-line with liquid water and freezing the water in place. In this example, the fill line helps to insure the battery container is not over-filled with liquid water that will expand when frozen and damage the container. Or the body may be filled to the fill-line with pre-frozen water such as crushed ice or ice packs. Of course, other types of thermal mass may be used with battery container 64 to make a thermal battery, such as dry ice, gel packs, or phase change materials other than water. In one embodiment, deuterium oxide ($D_2O$), also referred to as heavy water, is used as the thermal mass 66. $D_2O$ has a heat of fusion slightly higher than that of water on a volume basis, so filling the battery container with $D_2O$ at the same fill level as water results in a mass of phase change material that requires more energy to fully melt. In addition, $D_2O$ has a melting point of about 3.8° C. so that during its solid-liquid phase change it is above the freezing point of water, providing further protection to the contents of the contents container with regard to freezing. Any mixture of plain water and $D_2O$ may be used as well, to customize the phase change temperature, for example. $D_2O$ may also be included with the moderator material previously described in conjunction with the thermal moderator of FIG. 2 to take advantage of its particular thermal properties.

The operation of the above-described storage system with passive thermal moderators can be described by example where the stored contents must be kept in a temperature range from 2° C. to 8° C., the exterior environment is at a temperature higher than 8° C., and the thermal mass in the thermal batteries is wet ice that has been frozen and stored at a temperature less than 0° C. prior to use in the thermal batteries. At these conditions, three distinct transition periods occur with respect to the thermal batteries. The first transition period is during the time the ice changes temperature from its initial temperature, such as about −20° C., to its melting point (phase change temperature) of 0° C. The second transition period is during the time the ice is changing phase from solid to liquid. The third transition period is during the time the liquid water is increasing in temperature above 0° C. During the first transition period, the ice will absorb energy based on its specific heat capacity of 2.05 kJ/kg-K. In other words, it will absorb 41.0 kJ/kg during a temperature change from −20° C. to 0° C. During the second transition period, the ice will absorb energy based on its heat of fusion of 334 kJ/kg as it melts at constant temperature. During the third transition period, the liquid water will absorb energy based on its specific heat capacity of 4.18 kJ/kg-K. In other words, it will absorb 33.4 kJ/kg during a temperature change from 0° C. to 8° C. Given a known mass of ice, the total amount of thermal energy each thermal battery can absorb when heated from a temperature of −20° C. to 8° C. can then be calculated. The first and second transition periods may be of particular concern since these are the periods in which the thermal batteries could inadvertently freeze the stored contents if thermal energy flow is not properly managed.

The rate at which each of these transitions occurs is dependent upon the associated R-values of the materials surrounding each thermal battery, the surface area through which the thermal energy flows at the particular R-value, and the temperature differentials surrounding the thermal battery. More precisely:

$$Q=(\Delta T)(A)/R,$$

where Q is the rate of thermal energy flow to or from a thermal battery in Watts or J/s, $\Delta T$ is the temperature differential between the energy source and the thermal battery in degrees Kelvin (or ° C.), A is the surface area in $m^2$, and R is the R-value in $m^2K/W$.

Each thermal battery of the above described storage system absorbs thermal energy from two sources. One source is the exterior environment, and the other source is the contents container. In the absence of the thermal moderators described above, the R-value of the storage container walls (due to their relative thickness and the insulating or super-insulating materials from which they may be constructed) may be at least two orders of magnitude higher than the combined R-value of the thermal battery container walls and the contents container walls so that a large majority of the thermal energy absorbed by the thermal batteries would be from the contents container due to the energy flow rate from the contents container being several times higher than the energy flow rate from the exterior environment to the thermal batteries.

Figures 4, 5, 6, 7:
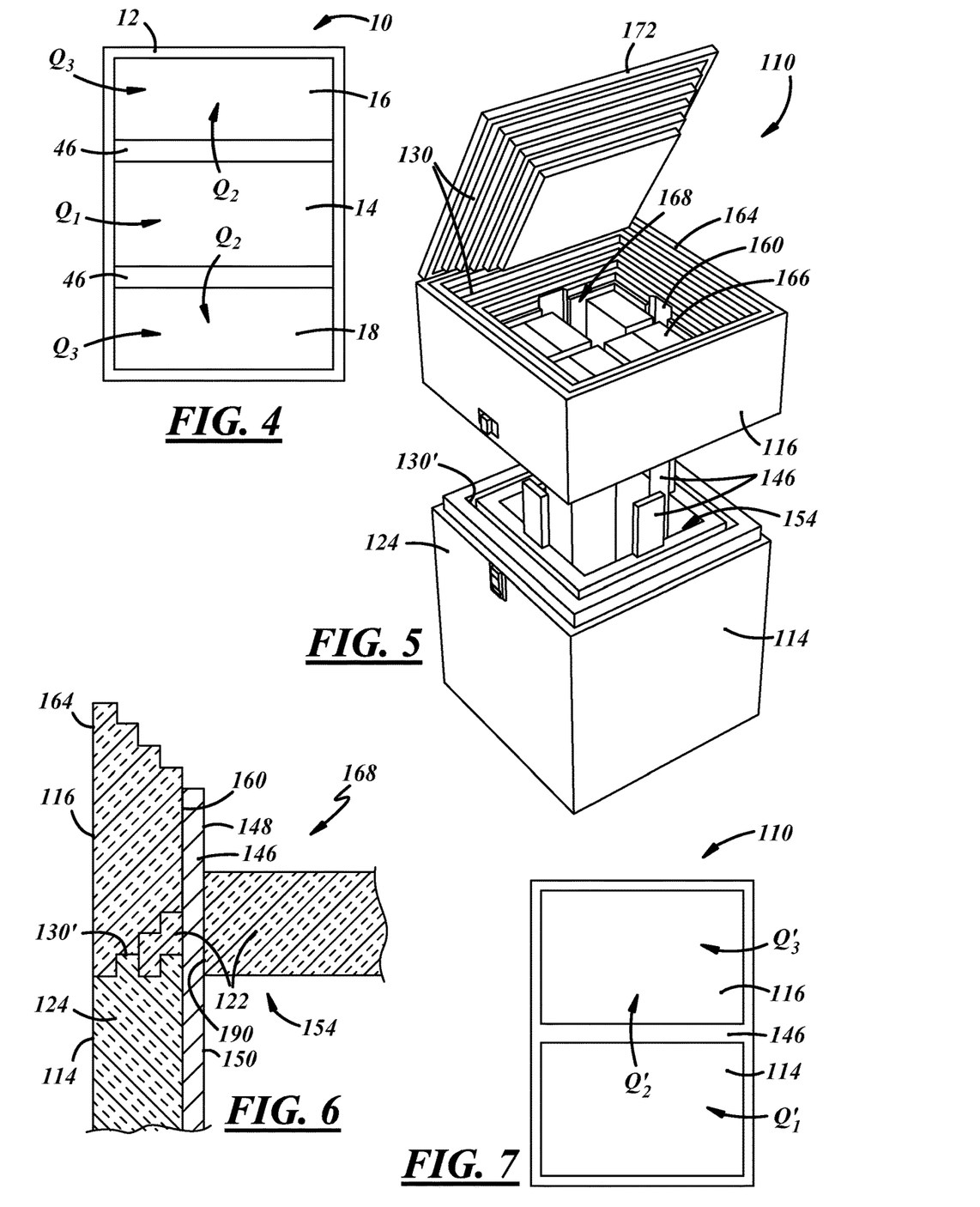
FIG. 4 is a schematic representation of the various thermal energy flow rates into and within the storage system of FIG. 1.
FIG. 5 is a perspective view of an exemplary storage system according to another embodiment, showing thermal moderators extending between a thermal battery and a complimentary contents container.
FIG. 6 is a partial cross-section of an exemplary joint between the thermal battery and the contents container similar to that of FIG. 5, taken through a thermal moderator.
FIG. 7 is a schematic representation of the various thermal energy flow rates into and within the storage system of FIG. 5.

The storage system described above, including thermal moderators as outlined, can help avoid this preferential energy flow from the contents container in multiple ways. FIG. 4 can be used to describe a method of balancing the thermal energy flow in the storage system 10 by customizing the thermal moderators in the system. FIG. 4 is a schematic representation of the storage system of FIG. 1, including storage container 12, contents container 14, and thermal batteries 16, 18, where contents container 14 includes thermal moderators 46 arranged between it and each thermal battery. Three thermal energy flow rates are represented by arrows in FIG. 4. $Q_1$ is the thermal energy flow rate between the external environment and the contents container 14; $Q_2$ is the thermal energy flow rate between the contents container 14 and each of the thermal batteries 16, 18; and $Q_3$ is the thermal energy flow rate between the external environment and each of the thermal batteries 16, 18. As described previously, a majority of the energy absorption per unit mass by the thermal batteries 16, 18 occurs during the second transition period of the thermal batteries—i.e., during the phase change of the thermal mass—particularly with wet ice as the phase change material. The thermal moderators 46 may be selected to balance the thermal energy flow within the storage system 10 and, in particular, into and out of contents container 14 during this period. In other words, referring to FIG. 4, $Q_1$, the energy flow rate into the contents container from the external environment, is preferably balanced with the total $Q_2$, the energy flow rate from the contents container to the thermal batteries 16, 18, by using thermal moderators with appropriately selected thermal properties.

$Q_1$ can be calculated using the R-value of the walls of storage container 12, the surface area of the side walls of the contents container 14, and the expected temperature differential from the exterior environment to the inside of the contents container 14. The R-value of the storage container walls may be treated as a constant, and so may the surface area of the contents container side walls. $\Delta T$ can be calculated using the initial temperature of the contents container when placed in the storage container 12 (e.g., somewhere between 2° C. and 8° C.) and the average expected temperature of the exterior environment.

$Q_2$ can be calculated in a similar manner. In this case $\Delta T$ is known, because the temperature of the thermal battery is, for example, 0° C., and the surface areas of the thermal communications areas described above, where the contents container 14 couples with the thermal batteries 16, 18, are known. Thus, setting the predicted $Q_1$ equal to the total $Q_2$, a desired R-value for each of the thermal moderators can be calculated to balance the thermal energy flow into and out of contents container 14 during the second transition period based almost entirely on the expected temperature of the external environment. For the thermal moderator 46 disposed between the contents container 14 and the lower thermal battery 18, the air gap between the top of the thermal mass and the thermal moderator should be taken into account when determining the required R-value for the lower thermal moderator—i.e., the thickness of the moderator material for the lower thermal moderator may be less than for the upper thermal moderator. With a modular system as disclosed herein, it is possible to have multiple different thermal moderators available for use in the storage system 10, each having an R-value tailored for use in a specific climate, for example.

The other transitional period of interest for the thermal batteries is the first transitional period, during which the thermal mass is increasing in temperature from its frozen storage temperature to its melting point, such as from −20° C. to 0° C. as may be typical for wet ice. Having selected the R-value of the thermal moderators 46 based on the steady-state second transitional period where the thermal batteries 16, 18 are at a constant temperature, the thermal flow rates $Q_1$ and $Q_2$ during the first transition period are not balanced by the selected R-value alone. The imbalance will be such that more energy is absorbed from the contents container 14 by the thermal batteries 16, 18 than is absorbed by the contents container 14 from the external environment ($Q_2 > Q_1$). This is because $Q_1$ is the same in both the first and second transitional periods, but $Q_2$ is increased during the first transitional period due to the higher $\Delta T$ between the contents container 14 and the thermal batteries 16, 18. In fact $Q_2$ may be up to 15 times higher during the first transition period than during the second transition period, particularly when the thermal batteries 16, 18 are first introduced to the storage container 12 and put into contact with contents container 14.

One way to further lessen the risk of inadvertent freezing of the contents of the contents container 14 is to include a phase change material as part of the moderator material in the thermal batteries 16, 18. For example, including a small amount of liquid water with the moderator material can provide a source, other than the contents container, from which the thermal batteries can absorb thermal energy while in the first transitional period. The amount of water to be added to each thermal moderator 46 can be calculated so that the liquid water in the thermal moderator has reached 0° C. and enough additional energy has been removed from it at 0° C. so that it is just beginning to become completely solid at the same time the thermal batteries reach 0° C. For example, as already noted, for one wet ice thermal battery to rise in temperature from −20° C. to 0° C., 41 kJ/kg is required. For the liquid water in the thermal moderator associated with a particular thermal battery to lower in temperature from, for example, 2° C. (an exemplary starting temperature for the contents container 14 and its thermal moderators) to 0° C., 8.36 kJ/kg must be removed from it, after which 334 kJ/kg is required for it to completely change to the solid phase. In that case, the amount of water included with the moderator material in the thermal moderator should be about 12% of the mass of that in the associated thermal battery to maximize the use of the moderator material water during its phase change from liquid to solid. This is a conservative estimate that assumes that all of the energy required to raise the temperature of the thermal battery to 0° C. is absorbed from the associated thermal moderator and from no other source. In reality, though, some thermal energy may also be absorbed from the external environment by the thermal batteries ($Q_3$ in FIG. 4), lessening the amount of phase change material required in the thermal moderator. In either case, the contents container never reaches sub-zero temperatures, and the risk of inadvertent freezing of its contents is thereby significantly lessened.

The example presented above is a non-limiting one. The storage systems herein described and the techniques for selecting appropriate materials and material properties for balancing certain thermal energy flow rates may be used with equal success to maintain stored contents within other temperature ranges and in other expected environments. For example, an exemplary storage system may be configured to maintain its contents at a temperature higher than the surrounding environment and may include thermal mass at a temperature higher than that of the surrounding environment and higher than the desired temperature range, using thermal moderators to provide a known thermal energy flow rate from the thermal mass to the contents container. In fact, the storage systems disclosed here are particularly suitable for such versatility because of their modularity and ability to change individual components without changing the entire system structure.

Referring now to FIG. 5, another embodiment of a storage system 110 is shown that also includes thermal moderators that can allow the use of thermal mass having a phase change temperature outside of the desired storage temperature range for the stored contents, while minimizing or eliminating the risk of the temperature of the stored contents falling outside of that range. In this embodiment, the storage system 110 includes a thermally insulated contents container 114, an insulated thermal battery 116, and thermal moderators 146. Contents container 114 includes a bottom wall (not visible in FIG. 5) and one or more side walls 124. In this example, contents container 114 is rectangular on all sides and includes four upright sidewalls 124 that partially define a storage area 154 to hold the stored contents.

Thermal battery 116 includes insulated battery container 164 and thermal mass 166 included in a thermal mass storage area 168. Battery container 164 is similar in construction and complimentary in shape with the contents container 114 and in this embodiment is configured to be the cover or top wall of the contents container 114 so that a wall is shared between the contents container storage area 154 and the thermal mass storage area 168 when the thermal battery 116 and the contents container 114 are fit together. Battery container 164 also includes its own top wall or cover 172 in this embodiment that, together with its sidewalls and bottom, define the storage area 168 for thermal mass 166. Thermal mass 166 may include any of the previously described thermal mass components. Though shown with the thermal battery as the top component of the system 110, the relative position of the thermal battery 116 and the contents container 114 may be different so that the thermal battery is on the bottom, so that the thermal battery and contents container are side-by-side, or so that there are more than one each of thermal batteries and/or contents containers. The arrangement shown in FIG. 5 may be preferable due to the more convenient access to the thermal mass 166 for replacement when necessary and for other reasons such as the direction of thermal energy flow with respect to gravity or to restrict access to the contents container. Each of the containers 114, 164 may include latch components as shown to temporarily attach the containers together when they are fitted together. Of course, other temporary attachment means may be included as well. One or both of the containers may also include additional components not shown, such as carrying handles, wheels, aesthetic components, etc.

One or more of the walls of the containers 114 and 164 may be constructed to include any of a variety of insulating materials, preferably including super-insulating materials. In fact, each container 114, 164 may be described in a similar manner as storage container 12 of FIG. 1, including the description of complex edge profiles along certain wall edges that is also applicable to edges 130 and 130' shown in FIG. 5, for example. Turning now to FIG. 6 by way of example, the exterior surface of the bottom wall of the thermal battery container 164 includes complimentary shapes formed therein that mate with edges 130' of the sidewalls 124 of contents container 114 when the containers are fit together. The interior surfaces of one or more of the walls of each container 114, 164 may include slots 160 to accommodate the thermal moderators 146 as shown. The slots 160 may be recessed areas in the walls as shown, they may have cross-sections defined within the thickness of the walls, or they may be omitted entirely. Slots 160 of the thermal battery container 164 extend completely through the bottom wall 122 of battery container 164 to form openings 190 to allow the thermal moderators to extend between the thermal mass storage area 168 and the contents container storage area 154.

Thermal moderators 146 are included to provide a known thermal energy flow rate between the contents container 114 and the thermal battery 116. More particularly, they provide thermal communication between the storage areas 154 and 168 of the respective components. In this embodiment, the thermal moderators are heat pipes. Generally, heat pipes are thermally conductive components that include an internal fluid, the fluid being selected such that its liquid-vapor phase change temperature is between the temperatures of the two surfaces or regions corresponding to opposite ends of the heat pipe when in use. The internal fluid absorbs thermal energy as a liquid at a first end of the heat pipe; changes to a vapor; carries the absorbed thermal energy toward a second, cooler end of the heat pipe; releases thermal energy at the second end by condensing to its liquid phase; and returns to the higher temperature end, by gravity or through capillary action, to begin a new thermal cycle. Heat pipes are able to transfer thermal energy from one end to the other at a rate higher than the thermal conductivity of the heat pipe material would normally allow due to their ability to carry and transfer this additional thermal energy via fluid phase changes. Heat pipes can additionally be customized to have a particular effective thermal conductivity or thermal energy flow rate by customizing the type of internal fluid or mixture of fluids and/or by varying the internal pressure of the heat pipe.

In the embodiment shown in FIGS. 5 and 6, heat pipes 146 are disposed in the slots 160 formed in the walls of the contents container, and may be fitted so that they are interchangeable with other heat pipes. One heat pipe 146 is shown along each wall, but the number required may vary. Each heat pipe is provided such that it has a particular thermal energy flow rate when one end is disposed in the storage area 154 of the contents container that is within a certain temperature range (such as 2° C. to 8° C.) and the other end is disposed in the storage area 168 of the thermal battery container that is at another temperature; typically the phase change temperature of the thermal mass (such as 0° C. for water) where a phase change material is included. Each heat pipe includes a thermal communication area 148, 150 at each end. As shown in FIG. 6, thermal communication area 148 is the surface of heat pipe 146 facing the thermal mass storage area 168 and thermal communication area 150 is the surface of heat pipe 146 facing the contents storage area 154.

The desired thermal energy transfer rate for each thermal moderator (heat pipe) 146 can be determined in a similar fashion as with the thermal moderators of FIG. 4. A schematic representation of the storage system 110 is shown in FIG. 7, for example, depicting thermal energy flow rates into, out of, and within the system 110. The FIG. 7 schematic is similar to that of FIG. 4 except that contents container 114 has only one thermal battery 116 in thermal communication with it through thermal moderator 146, where element 146 in FIG. 6 represents all of the thermal moderators of system 110 taken together. $Q_1'$ is the thermal energy flow rate between the external environment and the contents container 114; $Q_2'$ is the thermal energy flow rate between the contents container 114 and the thermal battery 116; and $Q_3'$ is the thermal energy flow rate between the external environment and the thermal battery 116. As before, during the second transition period of the phase change material in the thermal battery 116, the objective is to balance $Q_1'$ with $Q_2'$ using the thermal moderators 146.

$Q_1'$ can be calculated using the R-value of the walls of contents container 114, the surface area of the side walls and bottom of the storage area 126 of contents container 114, and the expected temperature differential from the exterior environment to the storage area of the contents container 114. To balance $Q_1'$ with $Q_2'$, heat pipes 146 are selected such that the sum of their individual thermal energy flow rates, when added to the thermal energy flow rate through the insulated bottom wall 122 of the battery container are equalized. Thus, the thermal moderators can be specified to balance the thermal energy flow into and out of contents container 114 during the second transition period based almost entirely on the expected temperature of the external environment. System 110 may also be modular, with the possibility of fitting various heat pipes with different thermal energy flow rates into the same slots 160 and the ability to exchange thermal batteries or contents containers. The particular embodiment of FIGS. 5 and 6 does not include provisions necessarily designed to retard thermal energy flow from the contents container to the thermal battery during the first transition period, when the phase change material of the thermal battery is warming from its frozen storage temperature to its melting point, such as from −20° C. to 0° C. as may be typical for wet ice. However, with this particular embodiment, the thermal communications areas 148, 150 of the thermal moderators 146 are not in direct contact with either the thermal mass 166 or the contents, reducing the likelihood of inadvertent freezing of the stored contents.

Skilled artisans will appreciate that, as used above, terms such as "balanced," "equal," and related terms, when used to refer to different thermal energy flow rates within the disclosed storage systems and between the storage systems and the surrounding environment, are not meant to describe values that are exactly equal to one another. For example, the temperature of the environment outside of the storage system may certainly vary, and calculations used to determine appropriate material properties for their thermal moderators may use average values in many cases. R-values are also known to vary with temperature and may also be averaged over their expected use temperatures, for example. Thermal energy flow is known to be a complex phenomenon, and the inventions claimed below are not limited to exact values where such terms are used.

It is to be understood that the foregoing is a description of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "for instance," "such as," and "like," and the verbs "comprising," "having," "including," and their other verb forms, when used in conjunction with a listing of one or more components or other items, are each to be construed as open-ended, meaning that that the listing is not to be considered as excluding other, additional components or items. Other terms are to be construed using their broadest reasonable meaning unless they are used in a context that requires a different interpretation.

The invention claimed is:

1. A storage system, comprising:
 a thermally insulated storage container having a storage area and comprising one or more side walls that partly define the storage area, each of the side walls including a layer of insulating material;
 a contents container having a contents container storage area for temperature-sensitive items and sized to fit in the storage area of the thermally insulated storage container;
 one or more thermal batteries, each thermal battery including a thermal mass for increasing a total heat capacity of the storage system and each thermal battery being sized to fit in the storage area of the thermally insulated storage container such that the contents container and the one or more thermal batteries are stacked together in the storage area of the thermally insulated container, wherein the thermal mass comprises a phase change material; and
 a plurality of passive thermal moderators having a plurality of different R-values, wherein the plurality of thermal moderators comprises interchangeable and modular components of the storage system, each passive thermal moderator shaped to be in thermal communication with the storage area of the contents container via a first thermal communication area having a first surface area and with one of the one or more thermal batteries via a second thermal communication area having a second surface area,
 wherein a first one of the thermal moderators of the plurality of thermal moderators configured to be positioned between the contents container storage area and each thermal battery when the storage system is used in a first environment having a first temperature, the first thermal moderator having a first R-value calculated and provided to balance a thermal energy flow rate between the storage area of the contents container and the one or more thermal batteries with a thermal energy flow rate between the storage area of the contents container and the first environment during a phase change of the phase change material, and
 wherein a second one of the thermal moderators of the plurality of thermal moderators configured to be positioned between the contents container storage area and each thermal battery when the storage system is used in a second environment having a second and different temperature, the second thermal moderator having a different second R-value calculated and provided to balance the thermal energy flow rate between the storage area of the contents container and the one or more thermal batteries with a thermal energy flow rate between the storage area of the contents container and the second environment during a phase change of the phase change material, thereby maintaining a desired temperature in the storage area of the contents container via use of the first thermal moderator in the first environment and the second thermal moderator in the second environment and the respective balanced thermal energy flow rates in each of the different environments,
 wherein the thermal energy flow rate between the storage area of the contents container and the one or more thermal batteries is determined at the thermal communication areas and the thermal energy flow rate between the storage area of the contents container and each of the first and second environments is determined in part by the difference between the respective first and second temperatures outside of the storage system and the desired temperature in the storage area of the contents container.

2. The storage system of claim 1, wherein the storage container removably houses the contents container, each thermal battery, and the thermal moderator(s).

3. The storage system of claim 1, wherein the storage system is modular such that the contents container or each thermal battery or both are removable from the storage system and replaceable with another contents container or thermal battery or both.

4. The storage system of claim 1, wherein the contents container and each thermal battery are in physical contact with each other.

5. The storage system of claim 1, further comprising a layer of super-insulating material located between the contents container storage area and the thermal mass, wherein each thermal moderator transmits thermal energy from one side of the super-insulating layer to an opposite side of the super-insulating layer.

6. The storage system of claim 5, wherein at least one of the plurality of thermal moderators includes the layer of super-insulating material.

7. The storage system of claim 1, wherein at least one of the plurality of thermal moderators includes a phase change material.

8. The storage system of claim 7, wherein the phase change material of the at least one of the plurality of thermal moderators changes between solid and liquid phases during use.

9. The storage system of claim 7, wherein the phase change material of the at least one of the plurality of thermal moderators changes between liquid and vapor phases during use.

10. The storage system of claim 7, wherein the phase change material of the at least one of the plurality of thermal moderators includes water, D2O, or both.

11. The storage system of claim 1, wherein at least one of the plurality of thermal moderators is attached to the contents container.

12. The storage system of claim 1, wherein each thermal moderator includes a layer of super-insulating material and a phase change material, and wherein the phase change material of each thermal moderator is present in an amount sufficient to transfer an amount of thermal energy between the phase change material of each thermal moderator and one of the one or more thermal batteries that changes a temperature of said one of the one or more thermal batteries from an initial thermal battery temperature to a phase change temperature of said one of the one or more thermal batteries, the amount of thermal energy being about the same amount of thermal energy required for the amount of phase change material to change phases.

13. The storage system of claim 1, wherein the plurality of thermal moderators includes a heat pipe.

14. The storage system of claim 1, wherein the one or more thermal batteries includes two thermal batteries; and the plurality of thermal moderators includes two thermal moderators, each one of the two thermal moderators being in thermal communication with the contents container and with one of the two thermal batteries.

15. The storage system of claim 1, wherein the thermal mass is wet ice and the desired temperature is above the freezing point of the wet ice.

16. The storage system of claim 1, wherein the thermal mass includes D2O.

17. The storage system of claim 1, further comprising an insert located in the storage area to accommodate and secure items when they are placed in the storage area.

18. The storage system of claim 1, wherein the thermal moderator includes a first end that extends into the contents container storage area and a second end that extends into a thermal mass storage area of the one or more thermal batteries.

19. The storage system of claim 18, wherein the thermal moderator extends through an opening in the layer of super-insulating material.

20. The storage system of claim 19, wherein the contents container and one of the one or more thermal batteries share a wall that includes the layer of super-insulating material.

21. The storage system of claim 20, wherein the thermal moderator is a heat pipe.

22. A storage system, comprising:
a contents storage area for holding temperature-sensitive items;
a thermal mass storage area for holding a thermal mass and being separate from the contents storage area;
a plurality of walls arranged to isolate each of the storage areas from an environment outside of the storage system, each wall including a layer of insulating material; and
a passive thermal moderator with a layer of super-insulating material and a thermal communication area defined by a surface area through which a majority of a thermal energy transferred between the storage areas is transferred, the layer of super-insulating material being located between the storage areas and the passive thermal moderator being constructed and arranged to transfer thermal energy between the storage areas via the thermal communication area and through the layer of super-insulating material, wherein, when the thermal mass is placed in the thermal mass storage area, the thermal moderator provides a pre-determined thermal energy flow rate between the thermal mass and the contents storage area that approximates a thermal energy flow rate through said plurality of walls between the environment outside of the storage system and the contents storage area during a phase change of the thermal mass, wherein the pre-determined thermal energy flow rate is defined as:

$$Q=(11T)(A)/R,$$

wherein 11T is the difference between the phase change temperature of the thermal mass and a desired temperature of said contents storage area, A is said thermal communication area, and R is the R-value of the super-insulating material.

23. The storage system of claim 22, further comprising:
a contents container that includes a body, a cover, and the contents storage area, wherein the contents storage area is between the body and the cover of the contents container;
a thermal battery that includes a body, a cover, and the thermal mass storage area, wherein the thermal mass storage area is between the body and the cover of the thermal battery; and
a storage container having a storage area defined by the plurality of walls, wherein the contents container and the thermal battery fit inside the storage area of the storage container.

24. The storage system of claim 23, wherein the thermal moderator includes the super-insulating layer and is configured to fit between the contents storage area and the thermal mass storage area.

25. The storage system of claim 24, wherein the thermal moderator is attached to the contents container or the thermal battery.

26. The storage system of claim 25, wherein the thermal moderator is located at the body of the contents container and the system further comprises another thermal moderator that includes a layer of super-insulating material located at the cover of the contents container, wherein, when the the thermal mass is placed in the thermal mass storage area, the thermal moderators together have the pre-determined thermal energy flow rate between the thermal mass and contents storage area that approximates a thermal energy flow rate between the environment outside of the storage system and the contents storage area during a phase change of the thermal mass.

27. The storage system of claim 26, wherein each thermal moderator further comprises a phase change material.

28. The storage system of claim 22, further comprising:
a contents container at least partially defined by some of the plurality of walls, wherein the contents container includes the contents storage area; and
a thermal battery at least partially defined by some of the plurality of walls, wherein the thermal battery includes the thermal mass storage area;
wherein the contents container and the thermal battery are configured to fit together with the layer of super-insulating material between the storage areas.

* * * * *